(12) United States Patent
Lin et al.

(10) Patent No.: US 6,292,260 B1
(45) Date of Patent: Sep. 18, 2001

(54) SYSTEM AND METHOD OF OPTICALLY INSPECTING SURFACE STRUCTURES ON AN OBJECT

(75) Inventors: Youling Lin; Charles Harris, both of Dallas; Max Guest, Plano; George C. Epp, Van Austyne, all of TX (US)

(73) Assignee: ISOA, Inc., Richardson, TX (US)

( * ) Notice: Subject to any disclaimer, the term of this patent is extended or adjusted under 35 U.S.C. 154(b) by 0 days.

(21) Appl. No.: 09/338,880

(22) Filed: Jun. 23, 1999

Related U.S. Application Data

(60) Provisional application No. 60/053,090, filed on Jul. 3, 1997.

(51) Int. Cl.⁷ .................................................. G01N 21/00
(52) U.S. Cl. ..................................... 356/237.4; 356/237.5
(58) Field of Search ................................. 356/237.1, 237.2, 356/237.3, 237.4, 237.5, 239.1, 394, 338; 250/572; 348/125, 126, 128; 382/141, 147, 149

(56) References Cited

U.S. PATENT DOCUMENTS

| | | | |
|---|---|---|---|
| 4,595,289 | * 6/1986 | Feldman et al. | 356/446 |
| 4,614,427 | * 9/1986 | Koizumi et al. | 356/237 |
| 5,046,847 | * 9/1991 | Nakata et al. | 356/338 |
| 5,818,576 | * 10/1998 | Morishige et al. | 356/237.1 |
| 5,822,055 | * 10/1998 | Tsai et al. | 356/239.1 |

* cited by examiner

*Primary Examiner*—Hoa Q. Pham
(74) *Attorney, Agent, or Firm*—Smith, Danamraj & Youst, P.C.

(57) ABSTRACT

A system and method of optically inspecting structures on the surface of an object, such as a semiconductor wafer. A platform is used to support the object under examination, and provided thereat are lights or other energy sources for illumination disposed at a selected angular orientation. Optimum illumination is achieved by orienting two opposing lateral energy sources to direct energy along the surface of the object at a very low angle, and using them in conjunction with a coaxial light source that emits energy, which is directed downward toward the surface. Energy reflected back from the surface is captured as an image by a suitable device such as a CCD camera. The lighting may be controlled by an attached computer, which can also be used to process and store the captured image and analyze it to detect and catagorize defects in the object being inspected.

15 Claims, 4 Drawing Sheets

SYSTEM AND METHOD OF OPTICALLY INSPECTING SURFACE STRUCTURES ON AN OBJECT

RELATED APPLICATIONS

This application is related to the following applications: U.S. Provisional Application Ser. No. 60/053,090, entitled System and Method of Optically Inspecting Manufactured Devices, filed Jul. 3, 1997; U.S. patent application Ser. No. 09/262,603, entitled System and Method of Optically Inspecting Structures on an Object, filed Mar. 4, 1999; U.S. patent application Ser. No. 09/074,301, entitled System and Method of Optically Inspecting Manufactured Devices, filed May 6, 1998; U.S. patent application Ser. No. 08/866,553, entitled System and Method for Circuit Repair, filed May 30, 1997; U.S. patent application Ser. No. 08/867,154, entitled System and Method for Defect Characterization and/or Diagnosis, filed May 30, 1997; U.S. patent application Ser. No. 08/866,771, entitled System and Method for Knowledge base Generation and Management, filed May 30, 1997.

Reference is also made to the following pending applications, each of which is incorporated by reference: U.S. patent application Ser. No. 08/186,691, entitled Apparatus and Method for Aligning and Measuring Misregistration, filed Jan. 24, 1994; U.S. Pat. No. 5,696,835, entitled Apparatus and Method for Aligning and Measuring Misregistration, which issued on Dec. 9, 1997; U.S. Pat. No. 5,703,969 entitled System and Method for Recognizing Visual indicia, which issued on Dec. 30, 1997; and U.S. Pat. No. 6,014,461, entitled Apparatus and Method for Automated Knowledgebased Object Identification, which issued on Jan. 11, 2000.

BACKGROUND OF THE INVENTION

1. Technical Field of the Invention

The present invention relates to the inspection of surface structures on an object and, more specifically, to a system and method for optically inspecting the surface of an object having surface structures thereon.

2. Description of Related Art

Optical inspection of an article of manufacture encompasses a variety of techniques that make use of the patterns produced by energy reflecting off (or passing through) the object being inspected. These reflections constitute an image that can be examined, compared with other images, stored, and otherwise analyzed. Examination may be performed by the human eye, with or without the aid of a magnifying device, such as a microscope. Or the image may be 'captured' by a camera and converted directly into electronic data for storage and analysis, either immediately or at some time in the future. In the manufacturing process, optical inspection can be done for the purpose of final acceptance or rejection, or as an intermediate step so that correctable defects can be remedied.

An example of a useful application of the present invention is the inspection of semiconductor wafers ("wafers"), both during and after the manufacturing process. Semiconductor wafers are slices of a semiconducting material, such as silicon, that are repeatedly coated, treated, and etched away in selected areas to form small (usually very small) interconnected electronic devices, such as transistors. A set of thousands, even millions of these interconnected devices is then separated from other sets formed on the wafer and encased in a package to form what is commonly referred to as a "chip". Chips can contain a very large number of electrical circuits and are used in a wide variety of applications. A single such chip, for example, one called a microprocessor, forms the "brains" of a modern personal computer.

A single wafer can serve as the base for forming several, or even hundreds of such devices. In order to transform a wafer into a set of microprocessors or other electronic devices, the wafer undergoes several manufacturing steps. First, a wafer is cut from a crystal ingot (such as crystallized silicon), and an epitaxial layer (a single layer of silicon crystals) may typically be grown on it. The creation of an epitaxial layer is often followed by the growth of high quality oxides on the wafer surface in a process called oxidation. Next, the wafer undergoes several fabrication steps. Each fabrication step places a layer of ions or other materials into or on the wafer, or removes portions from it, in a predetermined geometric pattern so as to form a portion of an electronic circuit. When these fabrication steps are completed, the wafer surface typically possesses several functional microelectronic devices. Each area of the wafer that is to become a separate device is called a "die".

Common wafer fabrication steps include chemical vapor depositions (CVD), plasma-enhanced vapor depositions (PECVD), etches, ion implantations, diffusions, metalizations, or the growth of structures directly on the wafer. Naturally, these structures are quite small, and the successful completion of the fabrication steps depends largely on the ability to precisely control the geometric placement of gasses, ions, metals, or other deposition materials. The processes of etching, implanting, etc., must be done with sub-micron precision. The precise placement of ions, metals, gasses, or other deposits and removal of other materials is often achieved through a process called photolithography. Though photolithography is well known in the art of microelectronic device manufacturing, a brief description thereof is provided herein because the teachings of the present invention are more particularly exemplified in the context of semiconductor fabrication.

Photolithography is a process by which the wafer surface is selectively covered with a material called photoresist (or simply resist) so that subsequent processes of ion implantation, etching, etc., effect only certain areas. Using a technique similar to film development in photography, a geometric pattern is transferred from a negative known as a mask (also called a reticle) onto a wafer. Photoresist contains photoactive sensitizers, and exposing it to light (or other activating radiation) produces a chemical change. The pattern in the mask causes light passing through it to be selectively blocked out, in effect casting a precise shadow onto the resist. The desired chemical change then occurs in the exposed areas. This step of the process is called imaging.

The first step in photolithography, however, is the preparation of the wafer itself. The wafer is cleaned, and a thin layer of liquid photoresist is distributed evenly across the top surface of the wafer. The photoresist is dried, and then the wafer with the photoresist thereon is heated to vaporize any solvents. Imaging can now be performed. During the imaging step, the photoresist is exposed to a light source at a predetermined wavelength. The mask's pattern, like a photographic negative, is projected onto one portion of the wafer at a time by a precision optical device known as a "stepper", and the pattern is preserved on each die by the photoresist. There are different kinds of photoresist used in wafer manufacture, each having different properties. "Positive" photoresist, for example, is made soluble by exposure to the light, while "negative" photoresist is hardened.

The next step in photolithography is called development, where the wafer is flushed with a solvent that washes away certain portions of the photoresist. The types of solvents used also varies. One solvent will wash away the portions of positive photoresist that were exposed to the light, while another washes away the unexposed portions of negative photoresist. In either case, the development process leaves the geometric pattern of the mask (or its negative) on each die. The result is a series of "photoresist structures" that together constitute a developed photoresist layer.

By selectively covering portions of the semiconductor wafer with photoresist structures, the entire wafer can, in a subsequent fabrication step, be exposed to various chemicals, ions, metals, or etchings without affecting the entire areas under the photoresist structures. After each fabrication step has been completed, a wash step is executed. In the wash step, all remaining photoresist is washed away and the wafer is cleaned. Often, one or more additional fabrication steps will be needed, and, the wafer will then undergo further photolithography processes.

When all fabrication steps are complete, the electrical characteristics of each die are tested. Based on the results of these tests, the die are "binned" (i.e., they are classified as good or defective). The wafer is then sliced into separate dice which are sorted to discard defective ones. The good dice are then prepared for packaging.

As can be seen from this discussion, in order to correctly manufacture microelectronic devices, geometrically correct patterns of photoresist structures must be deposited on the wafer during fabrication. And correct geometric patterning is dependent upon properly imaging and developing photoresist layers.

Each fabrication step is expensive and adds significantly to the cost of the semiconductor wafer. Furthermore, fabrication steps such as etching and ion implantation are difficult, if not impossible, to reverse in any cost-effective way. By contrast, photoresist structures can be removed quickly and with minimal disturbance to the underlying wafer structures. Thus, it is desirable to detect defects in the developed photoresist prior to performing a fabrication step. Photoresist defects are those anomalies that will result in impaired or altered electrical characteristics when fabrication of the die is complete, causing it to be rejected. Common photoresist defects include alignment errors, missing photoresist structures, contamination, and skewed photoresist.

If a defect can be detected in the developed photoresist layer prior to a fabrication step, one simply washes away the photoresist structures and develops another photoresist layer in place of the defective one. If the number of defects attributable to imperfections on the photoresist can be thereby reduced, the corresponding increase in die yield will result in considerable savings.

The most common method used to detect imperfections in a developed photoresist layer is optical inspection. Other available methods include electronic, ion beam, and X-ray imaging, but they are slower and more expensive than optical inspection because these imaging techniques illuminate and reconstruct only one point at a time. Laser imaging techniques that capture and compare the angle of reflection of laser beams can also be employed, but they lack comparable precision in reporting the position of defects.

Optical wafer inspection devices typically employ a support that holds a wafer under an overhead camera and one or more sources of light. In operation, the optical inspection device generally lights the wafer from several directions in order to provide full illumination, and the overhead camera captures a gray-scale (black-and-white) image of the wafer with a developed photoresist layer thereon. The captured image can then be analyzed in a variety of ways, generally with the aid of (or entirely by) a computer.

Although numerous advances have been recently achieved in the optical detection, analysis, and classification of defects, present systems still have disadvantages associated with efficiency, accuracy, and adaptability in manufacturing. Greater success in these areas can be obtained through the use of optimally configured illumination of the object being inspected. The system and method of the present invention have been discovered to lead to just such a result.

SUMMARY OF THE INVENTION

The present invention is directed to a system and method for inspecting surface structures on an object, for example, fabrication structures on the surface of a semiconductor wafer. In one aspect of the invention, the system comprises a platform that supports the object, a plurality of devices that emits visible light or other energy at a pre-determined angle onto a surface of the object to illuminate the surface and the structures thereon, an image-capturing device mounted at a pre-determined location for acquiring an image of the surface of the object or a portion thereof. A computer may also be present also in order to aid in analysis of the captured image.

The supporting inspection platform itself requires no particular configuration, but ideally it will allow for the efficient and reliable manipulation of the objects to be inspected. The source that emits light or other energy onto a surface of the object may emit, for example, laser light, X-rays, ion beams, electrons, or light in the infrared, ultraviolet, or visible spectrum. For convenience, the terms "light source" and "radiation source" will be used somewhat interchangeably in this discussion with the understanding that the present invention can be implemented with various forms of energy. The light sources can be adjustably mounted onto the support in any fashion consistent with the configuration of the present invention. Favorable results of the present invention are advantageously and optimally obtained when two low-angle opposing lateral sources are used in conjunction with a coaxial light source.

In one embodiment of the present invention, the opposing side sources are directed generally toward each other along the surface of the object, while the coaxial source emits energy in a direction generally perpendicular to the surface being examined. In another embodiment, a reflective surface allows the coaxial energy to originate from a source mounted on the side of the support, while still being directed downward toward the object surface. The image-capturing device is mounted above the surface in such a position as to enable it to capture an image of the desired area.

In another aspect, the present invention is directed to a method of inspecting an object surface having a structure on it. The method includes the steps of shining light or other energy across the object surface using two opposing sources provided laterally and a coaxial light source, and then capturing an image of the object or a portion thereof. The method further includes processing and analysis of the captured image to determine if defects exist, including using a computer to compare the captured image with an image of a defect-free object. The computer may also perform Automatic Defect Classification (ADC), direct repairs, and store the analyzed data in a knowledgebase for future reference.

Whenever a comparison is performed between an image of the object being inspected and a defect-free object image, the latter may be generated artificially, for example by Computer Aided Drafting, or by capturing the image of an object known to be free from defect and storing its image in a form suitable for comparison. "Defect-free" is used here to describe a condition of being, while not necessarily perfect, at least free from defects of a number or magnitude outside of the specific inspection tolerances.

BRIEF DESCRIPTION OF THE DRAWINGS

The invention will be better understood and its numerous objects and advantages will become more apparent to those skilled in the art by reference to the following drawings, in conjunction with the accompanying specification, in which.

DETAILED DESCRIPTION OF A PREFERRED EMBODIMENT

The present invention provides a system and method of optically inspecting the surface of an object. The preferred embodiment is described as a system and method of optically inspecting photoresist structures on the surface of semiconductor wafer dice. By using a unique configuration of object illumination sources, the present invention achieves the result of defect detection more efficiently and accurately than can be obtained using conventional methods and systems.

Figure 1:
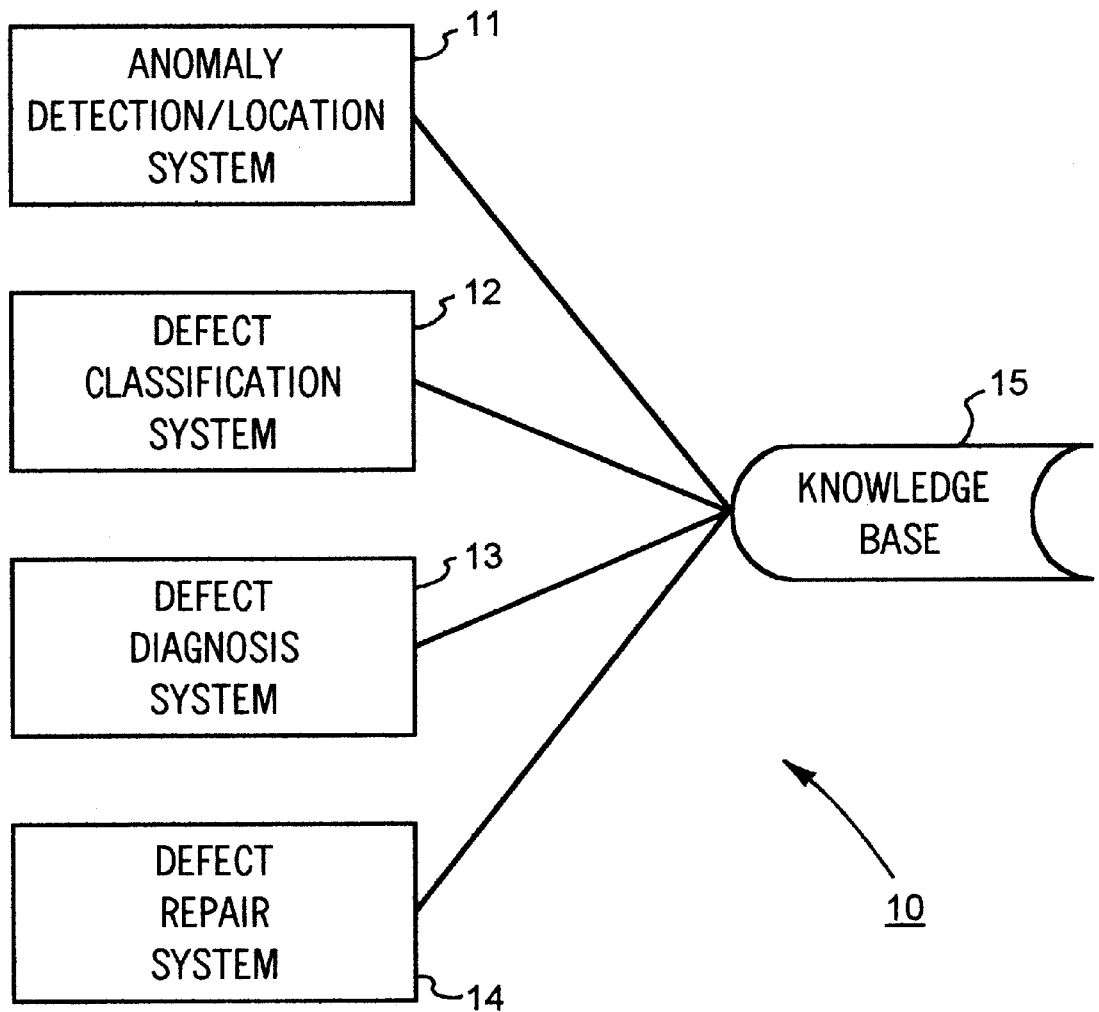
FIG. 1 is a functional block diagram of an integrated defect detection, classification, diagnosis, and repair system such as one for use in implementing the present invention.

In a preferred embodiment, the present invention is used in an optical Integrated Defect Detection, Classification, Diagnosis, and Repair (IDDCDR) system. FIG. 1 is a functional block diagram showing the basic components of a typical IDDCDR system 10. An anomaly detecting and locating inspection system 11 includes the actual components by which a manufactured object is positioned in a suitable environment, properly illuminated, and an image of the energy reflected off of the object is captured. Using this image, a defect classification system 12 determines the precise location and type of any anomaly detected (or determines that the anomaly is of a type not previously identified). Defect typing is performed with reference to a previously established (and continually supplemented) knowledgebase 15. After a defect has been found and categorized, a diagnosis system 13 attempts to identify the cause of the identified defect. Thereafter, suitable remedial action may be dictated by a defect repair system 14.

Figure 2:
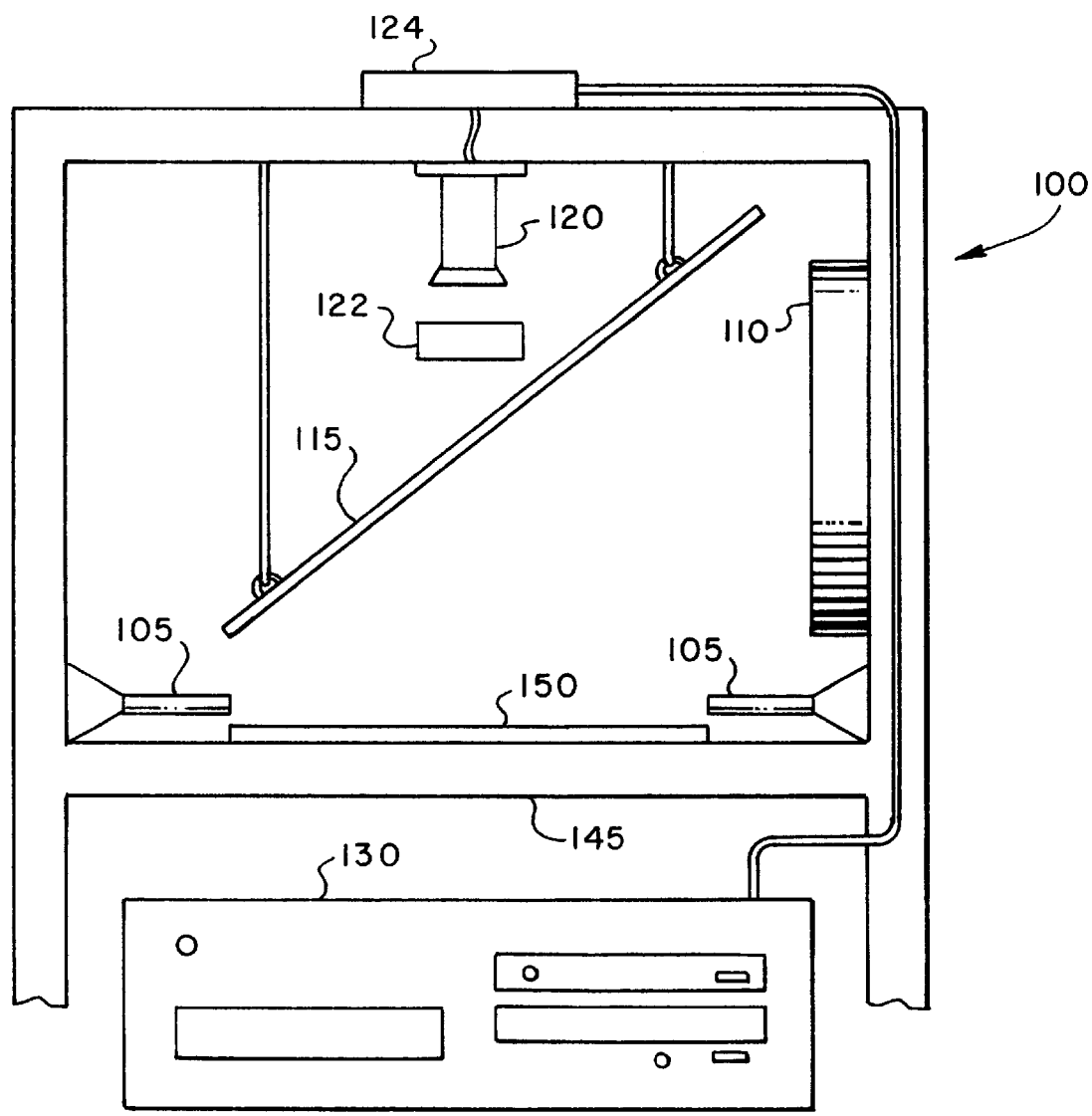
FIG. 2 depicts a view of a presently preferred exemplary embodiment of an optical inspection system provided in accordance with the teachings of present invention.

FIG. 2 depicts a view of a presently preferred exemplary embodiment of an optical inspection system 100 provided in accordance with the teachings of the present invention. It can be readily appreciated that the optical inspection system is preferably provided for inspecting surface defects of a wafer and forms a relevant portion of the anomaly detecting and locating system 10 shown in FIG. 1. Accordingly, the inspection system 100 may be used, in particular, to detect and locate photoresist anomalies in an integrated-circuit fabrication process. The inspection system 100 comprises one or more lateral radiation sources 105 (preferably, energy-emitting devices in the visible spectrum), a coaxial light source 110, a pass-through reflective surface 115, and a wafer support platform 145, which holds a wafer 150. Image-capturing device 120 is a sensor that captures an image of the surface of the wafer 150 (and the structures on it). A broad selection of suitable image capturing devices are available, including, for example, a line-scan camera or an area-scan camera. A suitable optical arrangement 122 is provided for appropriately manipulating the reflected radiation and may form a part of image-capturing device 120 or be a separate component. Optical arrangement 122 may, for example, comprise a lens system and be part of a microscope, but here is shown in position without a frame or additional lenses for illustrative clarity.

In this embodiment, a handling system (not shown) may also be used to place and remove wafers to and from supporting platform 145. If present, it may preferably comprise not only a wafer loading device, but also sensors to detect whether the wafer has been properly loaded and oriented, and a correction mechanism to adjust the placement of those that are not. A signal generator (not shown) is preferably also present to provide a specimen-ready signal to digitizer 124 or computer 130, as appropriate. Ensuring the correct positioning of an object to be inspected may also be accomplished by means of an orientation reference point (or points) placed on the object itself, the position of which can be detected by image-capturing device 120 so that necessary corrections can be indicated by an alarm or directed automatically by computer 130. In another embodiment, the object is put into place on a moving support platform that itself adjusts for proper placement and to facilitate inspection of the desired area.

Figure 3:
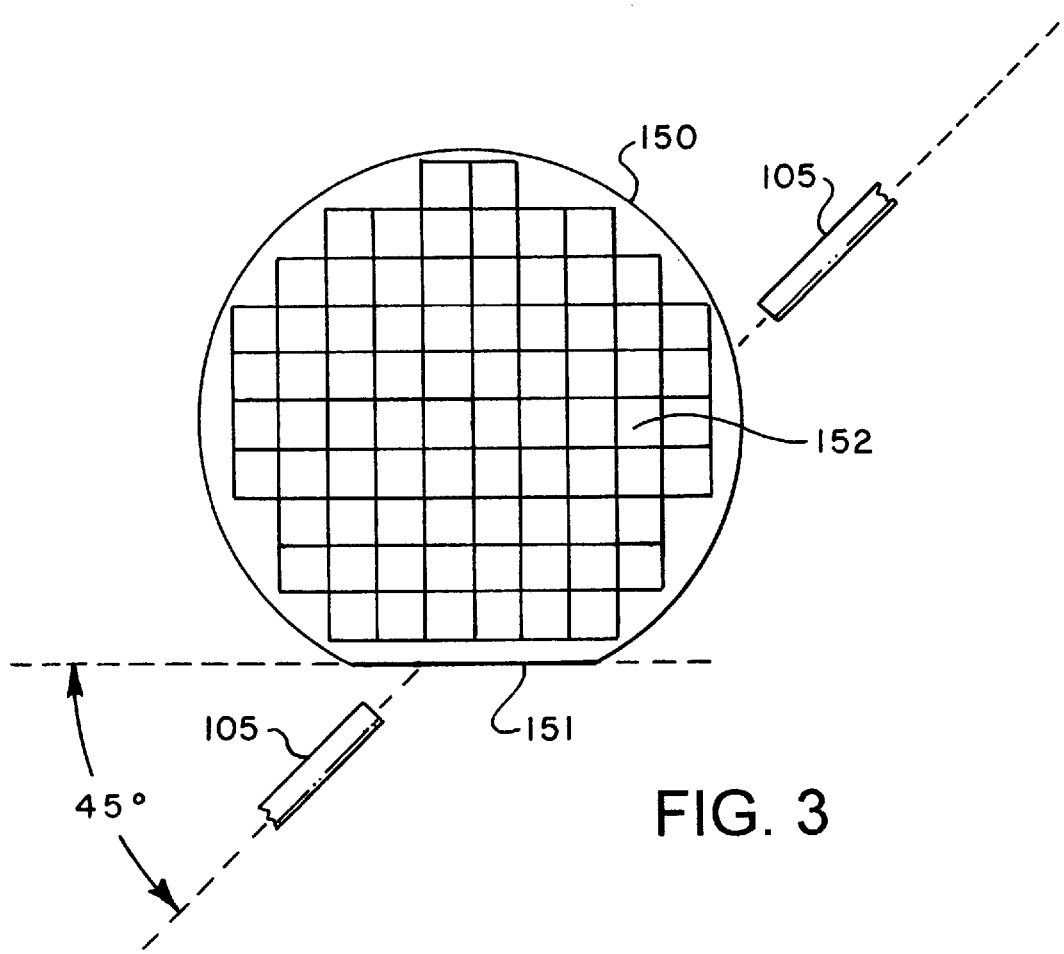
FIG. 3 is a top-plan view of a wafer illustrating a plurality of dice and showing a preferred arrangement of lateral energy sources.
Figure 4:
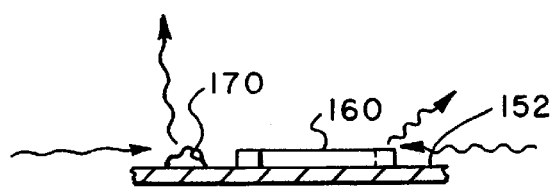
FIG. 4 is a front elevation view of a portion of the wafer showing a surface structure and an anomalous particle thereon.
Figure 5:
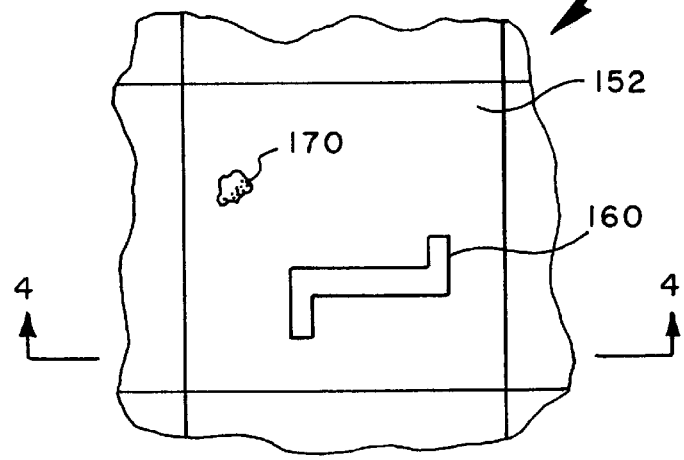
FIG. 5 is a top-plan view of the wafer portion depicted in FIG. 4.

FIG. 3 is a top-plan view of a wafer 150 illustrating a plurality of dice such as the die of wafer portion 152. FIGS. 4 and 5 are an enlarged side elevational view and top-plan view of a portion of the wafer shown in FIG. 3, including a wafer portion 152 having photoresist structure 160 and anomalous particle 170 thereon.

Continuing to refer to FIG. 2, as previously discussed, the lateral radiation sources 105 and coaxial source 10 may emit light or other energy onto the surface of the wafer, for example, laser light, X-rays, ion beams, scanning electrons, or light in the infrared, ultraviolet, or visible spectrum. The efficiency of the present invention, however, and its ability to detect structure edges, such as photoresist island edges, is related to the ability to produce crisp, sharp component edges under the image capturing device 120. Therefore, in this embodiment, the lateral radiation sources 105 and coaxial source 10 are preferably coherent light sources having minimally diffuse emitted light. In one embodiment, a plurality of fiber-optic lines may be employed as part of the lateral radiation sources 105 to carry and direct the emitted light. Alternatively, a single source may supply both lines transmitting the lateral illumination. It should be noted that in general, when a plurality of lights, sources, or energy-emitting devices are discussed in the context of the teachings of the present invention, it is equally acceptable to use instead a lesser number of generating sources and divide and transmit or redirect the produced energy to appropriately illuminate the surface being inspected. For example, as shown in FIG. 2, the pass-through reflective surface 115 is used to redirect the light from source 110 in a coaxial direction in reference to the planar surface of the wafer 150.

Lateral radiation sources 105 emit light energy directed in substantially opposite directions and parallel to the object surface. However, the light need not emanate exactly parallel to, or co-planar with, the surface, and a small angle downward toward the surface may be necessary to achieve proper illumination under some circumstances. Similarly, the opposing lateral radiation sources 105 need not be positioned exactly at 180° with respect to each other to obtain the advantages of the present invention. While minor adjustments may have to be made in some instances, however, using a relative angle that approaches direct opposition as closely as possible (viewed from above) is expected to yield favorable results.

Similarly, the coaxial light produced by source 110 should be directed toward the object surface in a direction as near perpendicular as possible, although minor deviation here is also tolerable. In one embodiment of the present invention, it is desirable to have the radiation sources adjustably mounted so that minor imprecision in the mounting apparatus can be corrected, or small deviations may be made to account for local conditions.

When the inspection system 100 is used for semiconductor wafer inspection, as it is shown in the embodiment depicted in FIG. 2, it is preferred that opposing lateral radiation sources 105 be positioned at substantially 45° with respect to a reference edge of the wafer 150 such as, for example, a flat 151, a straight edge typically formed in otherwise round production wafers. This arrangement is depicted in FIG. 3. Through innovation and empirical analysis, this angle has been found to result in optimum illumination for inspection and defect identification. As is known in the art, properly disposed fabrication structures will generally have sides and edges that are oriented in a regular fashion (e.g., parallel or perpendicular) with respect to the flat 151. FIGS. 4 and 5 depict views of a wafer portion 152 having a properly deposited fabrication structure 160 thereon in contrast to a surface defect such as, for example, a particulate object 170 having irregular contours and surfaces. As can be readily seen, regular fabrication structures generally have horizontal top surfaces and vertical walls also. This expected configuration of proper structures means that the illumination configuration of the present invention will have the effect of highlighting surface anomalies (such as the particle 170 in FIGS. 4 and 5) in the reflected radiation from the object surface, so that their presence can be quickly and easily detected by the image-capturing device 120. When objects other than semiconductor wafers are inspected using the system or method of the present invention, similar desirable results are expected if lateral sources 105 are likewise oriented at an angle of substantially 45° to the faces or edges of structures located on the object surface.

The image-capturing device 120 is preferably a single line-scan or area-scan overhead camera. A suitable image-capturing device is the XC003 3CCD (Charge Coupled Device) Area-Scan Color Camera available from the Sony Corporation. Shown in FIG. 2 as mounted directly above wafer 150, image-capturing device 120 can actually be mounted in any position allowing it to capture a useable image of the object being illuminated. The presence, position, and nature of pass-through reflective surface 115 will also influence the position of image-capturing device 120, as will the capabilities of device 120 itself. Digitizer 124 can be, for example, a frame grabber or other similar device that receives the image from image-capturing device 120 and converts it into a digital array of pixels or a pixel-based representation of the image. A pixel is one of numerous, very small logical divisions of the image, and digitizer 124 measures the intensity (e.g., light intensity) of the reflected energy for each pixel. Image pixel data can be stored for future use in memory associated with digitizer 124, computer 130, or with some other storage device.

Once the object surface has been illuminated in accordance with the present invention and a gray-scale image has been captured by device 120, a variety of techniques may be applied to examine and analyze it. These techniques can range from simple human-eye inspection of the captured image once it has been transferred to a monitor or still photograph, to sophisticated computer processing and analysis. To place the invention in context, some of these methods will be described briefly here.

Generally, a computer (such as, for example, computer 130 shown in FIG. 2) will be used as part of the inspection system 100 and method of the present invention. Computer 130 can be used to control the inspection process, for example dictating the rate at which objects are moved through the inspection area, the angle and intensity of the lighting, the focus of a camera lens, etc. A critical function of computer 130, however, is to facilitate generating an electronic representation of the captured image, and then to manipulate, store, and analyze it. The computer 130 may serve each of the systems of the IDDCDR 10 shown in FIG. 1, or each system may have its own computer, in which case it is preferable that each computer is part of an organized and coordinated network.

In general, a computer analysis of the captured reflective image of an illuminated object actually begins with the generation of a background basis for comparison. This can be done by building a file containing the appropriate attributes of a defect-free object and storing it in a knowledgebase associated with computer 130 or a separate network-connected computer. The term "knowledgebase" is used here because the defect and reference data associated with the present invention can, but does not have to be, stored in a traditional database. The knowledgebase may preferably comprise a portion of an Integrated Yield Production and Management System usable in a semiconductor fabrication line, and may employ predictive-corrective algorithms, etc. An example of alternative defect-related data indexing using computer operating system subdirectories is described in co-pending U.S. patent application Ser. No. 09/262,603, which is incorporated here by reference. However it is stored, this reference attribute file can be built using, for example, a CAD system. Alternatively, inspection system 100 can be used to illuminate an object of the kind to be inspected but that previously has been found to be defect-free. The captured image of the defect-free object is then processed in the same manner as is the inspected object image, and the resulting data stored for future use.

Captured images of inspected objects can be processed for computer comparison in different ways. In one embodiment, descriptive geometries of object surface structures reflected in the captured image can be obtained by symbolic decomposition of the image to produce a primitives-based representation of the image. A primitive is a compact unit of image-describing information. For example, a primitive for a line segment may include a start point, an end point, the light intensity to the left of the line segment, and the light intensity to the right of the line segment. A collection of primitives that completely describe a structure are called the structure's "grammar". Grammar, in other words, may be thought of as the symbolic representation of the structure it describes. In an embodiment of the present invention, the structure of the photoresist or other materials (such as metal or polyamide deposited on the wafer surface) detected by inspection system 100 will be completely described by image structure grammar expressed in terms of a small number of numeric primitives. Decomposition itself may be accomplished in several ways, such as those described in U.S. Pat. Nos. 5,515,453 and 5,553,168, and in U.S. patent applications Ser. Nos. 08/347,020, 08/867,156, and 09/262,603, all of which are incorporated here by reference.

Briefly, in one embodiment of the present invention, image decomposition is performed by systematically scanning the captured image for pixels having an intensity different from that of the background surface, that is, the structure-free portion of the object's surface. A variation in intensity, or gradient, indicates the edge of a structure, such as structure 160 or anomaly 170 shown in FIG. 5. When an edge is encountered the scan is altered so as to trace the boundaries of the detected structure. When this trace has been done, a set of descriptive primitives forming the grammar of the structure is stored and the systematic scan continues. Other structures encountered in the scan will also be traced, but gradients falling within previously traced grammars will generally not initiate a repetitive trace of a previously detected structure. The captured image and the reference image can then be compared and any differences noted. Differences rising to a certain order of magnitude will be classified as anomalies. The comparison can be made on a on a pixel-by-pixel basis, or by using the grammars and primitives if they are available. To increase precision and accuracy in defect detection, multiple images of an object may be captured, and the grammars for each synthesized and compared to filter out spurious defect indications. Capturing additional images from other illumination configurations may also aid in defect detection, but is not necessary to practice the present invention.

In one embodiment of the invention, when a defect is found the computer 130 (or a connected computer) can automatically classify it according to a stored index of defects in the knowledgebase. Defects are classified by comparing stored descriptive elements such as pixels, primitives, and grammars in a process similar to that by which the defect was found. If a particular defect has not been noted previously, the knowledgebase may be supplemented to include information about the new defect. A report can then be generated, ideally one that can be used for determining corrective measures to fix the defective object and to prevent such defects from recurring.

Based on the foregoing description, one of ordinary skill in the art should readily appreciate that the present invention advantageously provides a system and method for quickly and easily inspecting/identifying surface defects on a variety of object surfaces. The illumination system of the present invention is not only portable and cost-effective, but is also highly adaptable for in-line inspection of products on a manufacturing or fabrication line. Furthermore, the illumination systems described herein can be integrated with relative ease into a variety of known and hitherto unknown automated defect imaging systems such as those used in integrated yield management.

It is thus believed that the operation and construction of the present invention will be apparent from the foregoing description. While the system and method shown and described has been characterized as being preferred, it will be readily apparent that various changes and modifications could be made therein without departing from the scope of the invention as defined in the following claims.

What is claimed is:

1. A system for inspecting a surface of a semiconductor wafer having a straight side (flat), said system comprising:
   a support for supporting the wafer to be inspected;
   a first energy-emitting device mounted at a height above the support approximately equal to the height of the surface of the wafer to be inspected and directed to emit energy along and substantially parallel to the surface of the wafer, wherein said first energy-emitting device is positioned at an azimuth angle of substantially 45° relative to the flat;
   a second energy-emitting device mounted at a height above the support approximately equal to the height of the surface of the wafer to be inspected and directed to emit energy along and substantially parallel to the surface of the wafer, and in a direction substantially opposing that of said first energy-emitting device;
   a third energy-emitting device mounted at a height above the surface of the wafer for emitting energy directed toward and substantially perpendicular to the wafer surface to be inspected; and
   an image-capturing device aimed to capture an image of the surface as illuminated by the first, second, and third energy-emitting devices.

2. The system of claim 1, further comprising at least one reflective surface for directing the energy emitted by said third energy-emitting device toward and substantially perpendicular to the surface being inspected.

3. The system of claim 1, wherein said first energy-emitting device is selected from the group consisting of a visible light source, an infrared light source, an ultraviolet light source, an X-ray source, a focused ion beam source, and an electron source.

4. The system of claim 1, wherein said second energy-emitting device is selected from the group consisting of a visible light source, an infrared light source, an ultraviolet light source, an X-ray source, a focused ion beam source, and an electron source.

5. The system of claim 1, wherein said image-capturing device is selected from the group consisting of a line-scan camera and an area-scan camera.

6. The system of claim 1, further comprising means for recording the image captured by said image capturing device.

7. The system of claim 6, wherein said recording means is a computer.

8. The system of claim 7, wherein said computer further comprises software for manipulating image data.

9. The system of claim 8, further comprising a knowledgebase accessible by said computer for receiving and storing a defect-free reference image for comparison.

10. The system of claim 9, wherein said computer performs automatic defect classification for classifying any differences between the captured image associated with the object and the defect-free reference image.

11. The system of claim 8, wherein said computer is capable of generating structure grammar from the captured image.

12. A method of inspecting semiconductor wafer having a flat, the method comprising the steps of:
   supporting the wafer on an inspection platform;
   emitting energy from a first source along and substantially parallel to the wafer surface to be inspected, wherein the energy emitted from said first source is directed at an angle of substantially 45° relative to the flat;

emitting energy from a second source along and substantially parallel to the surface to be inspected and in a direction substantially opposing that of the energy emitted from a said first source;

emitting energy from a third source directed toward and substantially perpendicular to the surface to be inspected; and capturing an image of the illuminated surface.

13. The method of claim 12, further comprising the step of converting the captured image into a pixel-based image.

14. The method of claim 12, further comprising the steps of:

producing a captured-image surface structure map; and comparing said structure map it to a stored defect-free surface structure map.

15. The method of claim 14, further comprising the step of comparing a defect detected in said structure map comparison step to a knowledgebase of stored defect data for classification.

* * * * *